(12) United States Patent
Chouinard (10) Patent No.: US 7,223,283 B2
(45) Date of Patent: May 29, 2007

(54) STENT WITH IMPROVED FLEXIBILITY

(75) Inventor: Paul F. Chouinard, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 701 days.

(21) Appl. No.: 10/269,111

(22) Filed: Oct. 9, 2002

(65) Prior Publication Data

US 2004/0073290 A1 Apr. 15, 2004

(51) Int. Cl.
*A61F 2/86* (2006.01)
(52) U.S. Cl. ................................................ 623/1.15
(58) Field of Classification Search ............... 623/1.15, 623/1.2, 1.22, 1.16
See application file for complete search history.

(56) References Cited

U.S. PATENT DOCUMENTS

| | | | | |
|---|---|---|---|---|
| 5,716,365 | A | 2/1998 | Goicoechea et al. | 606/108 |
| 5,755,770 | A | 5/1998 | Ravenscroft | 623/1 |
| 5,824,046 | A | 10/1998 | Smith et al. | 623/1 |
| 5,895,407 | A | 4/1999 | Jayaraman | 606/198 |
| 6,017,365 | A | 1/2000 | Von Oepen | 623/1 |
| 6,022,371 | A * | 2/2000 | Killion | 606/198 |
| 6,162,245 | A | 12/2000 | Jayaraman | 623/1.15 |
| 6,206,911 | B1 | 3/2001 | Milo | 623/1.15 |
| 6,231,598 | B1 | 5/2001 | Berry et al. | 623/1.15 |
| 6,331,188 | B1 | 12/2001 | Lau et al. | 623/1.13 |
| 6,340,366 | B2 | 1/2002 | Wijay | 623/1.13 |
| 6,355,057 | B1 | 3/2002 | DeMarais et al. | 623/1.15 |
| 2002/0007212 | A1 | 1/2002 | Brown et al. | 623/1.1 |
| 2002/0022876 | A1 | 2/2002 | Richter et al. | 623/1.15 |
| 2002/0055770 | A1 | 5/2002 | Doran et al. | 623/1.15 |
| 2002/0111669 | A1 * | 8/2002 | Pazienza et al. | 623/1.15 |
| 2002/0120322 | A1 | 8/2002 | Thompson et al. | 623/1.11 |

FOREIGN PATENT DOCUMENTS

| | | |
|---|---|---|
| WO | 00/30563 | 6/2000 |
| WO | 01/32099 A2 | 5/2001 |
| WO | 01/58386 A1 | 8/2001 |
| WO | 02/060344 A2 | 8/2002 |

OTHER PUBLICATIONS

U.S. Appl. No. 10/063,179, filed Mar. 28, 2002, Gregorich et al.

* cited by examiner

*Primary Examiner*—Michael Thaler
(74) *Attorney, Agent, or Firm*—Vidas, Arrett & Steinkraus P.A.

(57) ABSTRACT

A stent comprises a plurality of connected serpentine circumferential bands. Adjacent serpentine circumferential bands are connected via a plurality of longitudinal connectors extending between peaks on one serpentine circumferential band and troughs on the serpentine circumferential band adjacent thereto. The struts of the serpentine bands are arranged such that on expansion of the stent, peaks and troughs which are substantially circumferentially aligned with one another, but not connected with one another, on adjacent serpentine circumferential bands are circumferentially displaced from one another.

10 Claims, 7 Drawing Sheets

STENT WITH IMPROVED FLEXIBILITY

BACKGROUND OF THE INVENTION

Stents are placed or implanted within a variety of bodily vessels including in coronary arteries, renal arteries, peripheral arteries including illiac arteries, arteries of the neck and cerebral arteries, veins, biliary ducts, urethras, fallopian tubes, bronchial tubes, the trachea, the esophagus and the prostate.

Stents are available in a wide range of designs. One popular stent design includes a plurality of serpentine rings having alternating peaks and troughs. Adjacent rings are interconnected via connecting elements. If adjacent rings are spaced too close together, however, binding, overlapping or interference can occur between adjacent rings on the inside of a bend due to the facing peaks and troughs moving toward each other and into contact.

There remains a need for innovative, flexible stents which are designed so that interference between adjacent rings does not substantially occur.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

All U.S. patents and applications and all other published documents mentioned anywhere in this application are incorporated herein by reference in their entirety.

SUMMARY OF THE INVENTION

In one embodiment, the invention is directed to a stent comprising at least two serpentine circumferential bands including a first serpentine circumferential band and a second serpentine circumferential band. Each serpentine circumferential band has alternating peaks and troughs. There is a plurality of unconnected peak-trough pairs with each unconnected peak-trough pair comprising a peak on the first serpentine circumferential band and a trough on the second serpentine circumferential band which is substantially circumferentially aligned with the peak when the stent is in an unexpanded configuration and desirably when it is in a delivery configuration on a catheter. The trough is not connected to the peak. There also is a plurality of connected peak-trough pairs with each connected peak-trough pair comprising a peak on the first serpentine circumferential band and a trough on the second serpentine circumferential band which is substantially circumferentially aligned with the peak when the stent is in an unexpanded configuration and desirably when it is in a delivery configuration on a catheter. The trough is connected to the peak. The distance along the first serpentine circumferential band between each peak of a connected peak-trough pair and an adjacent peak of an unconnected peak-trough pair differs from the distance along the second serpentine circumferential band between the trough of the connected-trough pair and an adjacent trough of an unconnected peak-trough pair, the adjacent peak substantially opposite the adjacent trough. As the stent expands, peaks and troughs of unconnected peak-trough pairs are displaced relative to one another about the circumference of the stent.

Desirably, the first and second serpentine circumferential bands are connected to one another via a plurality of longitudinal connectors.

Typically, the stent will have three or more of the serpentine circumferential bands, adjacent serpentine circumferential bands connected one to the other. There will be a plurality of unconnected peak-trough pairs along adjacent serpentine circumferential bands, each unconnected peak-trough pair comprising a peak on one serpentine circumferential band and a trough on the adjacent serpentine circumferential band which is substantially circumferentially aligned with the peak when the stent is in an unexpanded configuration, and desirably in a delivery configuration on a catheter, the trough not connected to the peak. There will also be a plurality of connected peak-trough pairs along adjacent serpentine circumferential bands, each connected peak-trough pair comprising a peak on one serpentine circumferential band and a trough on the adjacent serpentine circumferential band which is substantially circumferentially aligned with the peak when the stent is in an unexpanded configuration, and desirably in a delivery configuration on a catheter, the trough connected to the peak. The distance along a serpentine circumferential band between each peak of a connected peak-trough pair and an adjacent peak of an unconnected peak-trough pair differs from the distance along the adjacent serpentine circumferential band between the trough of the connected-trough pair and an adjacent trough of an unconnected peak-trough pair, the adjacent peak substantially opposite the adjacent trough.

The invention is also directed to a stent, comprising a plurality of serpentine circumferential bands comprising alternating peaks and troughs. Adjacent serpentine circumferential bands are connected to one another. The serpentine circumferential bands include a first serpentine circumferential band, a second serpentine circumferential band and a third serpentine circumferential band. The first serpentine circumferential band includes high peaks and low peaks. The second serpentine circumferential band includes high peaks and low peaks, high troughs and low troughs. The third serpentine circumferential band includes high troughs and low troughs. The high peaks of the first serpentine circumferential band are substantially circumferentially aligned with the low troughs of the second serpentine circumferential band and the low peaks of the first serpentine circumferential band are substantially circumferentially aligned with the high troughs of the second serpentine circumferential band. Also the high peaks of the second serpentine circumferential band are substantially circumferentially aligned with the low troughs of the third serpentine circumferential band and the low peaks of the second serpentine circumferential band are substantially circumferentially aligned with the high troughs of the third serpentine circumferential band. Desirably, the first serpentine circumferential band is interlaced with the second serpentine circumferential band and the second serpentine circumferential band is interlaced with the third serpentine circumferential band.

Desirably, adjacent serpentine circumferential bands are connected to one another via a plurality of longitudinal connectors extending between substantially circumferentially aligned peaks and troughs.

Typically, there will be a plurality of unconnected peak-trough pairs, each unconnected peak-trough pair comprising a peak on a serpentine circumferential band and a trough on the serpentine circumferential band adjacent thereto which is substantially circumferentially aligned with the peak when the stent is in an unexpanded configuration, and desirably in a delivery configuration on a catheter, the trough not connected to the peak. There will also be a plurality of connected peak-trough pairs, each connected peak-trough pair comprising a peak on a serpentine circumferential band and a trough on the serpentine circumferential band adjacent thereto which is substantially circumferentially aligned with the peak when the stent is in an unexpanded configuration, and desirably in a delivery configuration on a catheter, the trough connected to the peak. The distance along the serpentine circumferential band between each peak of a connected peak-trough pair and an adjacent peak of an unconnected peak-trough pair differs from the distance along the adjacent serpentine circumferential band between the trough of the connected-trough pair and an adjacent trough of an unconnected peak-trough pair, the adjacent peak substantially opposite the adjacent trough.

As the stent expands, peaks and troughs of unconnected peak-trough pairs are displaced relative to one another about the circumference of the stent.

The invention is also directed to a stent having a proximal end and a distal end comprising a plurality of connected serpentine circumferential bands. Each serpentine band comprises a plurality of struts arranged in alternating peaks and troughs. Adjacent serpentine circumferential bands are connected via a plurality of longitudinal connectors extending between peaks on one serpentine circumferential band and troughs on the serpentine circumferential band adjacent thereto. The struts of the serpentine bands are arranged such that on expansion of the stent, peaks and troughs which are substantially circumferentially aligned with one another, but not connected with one another, on adjacent serpentine circumferential bands are circumferentially displaced from one another. Typically, each band comprises a repeating pattern of three or more struts of different lengths. The struts of different lengths are also typically of different widths. Desirably, the stent is constructed and arranged to be self-expanding.

The invention is also directed to a stent comprising at least one circumferential serpentine band disposed about a longitudinal axis, the serpentine band comprising a plurality of struts, adjacent struts connected one to the other, the serpentine band having alternating peaks and troughs, the serpentine band including at least three peaks which are circumferentially and longitudinally offset from one another. Typically, the stent will comprise a plurality of the circumferential serpentine band, adjacent circumferential serpentine bands connected to one another. Desirably, adjacent circumferential serpentine bands are connected to one another via two or more longitudinal connectors. More desirably, the stent is constructed such that unconnected peaks and troughs which are substantially circumferentially aligned prior to expansion of the stent are circumferentially displaced from one another on expansion of the stent.

The invention is also directed to a stent comprising at least one serpentine circumferential band which comprises a repeat pattern of three or more struts of different lengths. Desirably, the stent comprises a plurality of the serpentine band, adjacent bands connected to one another. The struts are arranged in a pattern of alternating peaks and troughs.

The invention is also directed to a stent comprising at least two serpentine bands including a first serpentine band and a second serpentine band, each serpentine band having alternating peaks and troughs, the first serpentine band including connected peaks and unconnected peaks, the second serpentine band including connected troughs and unconnected troughs. The peaks of the first serpentine band are substantially longitudinally aligned with the troughs of the second serpentine band when the stent is in an unexpanded state, and desirably in a delivery configuration on a catheter. The connected peaks are connected to the connected troughs with connectors, each of the connectors having two ends which are substantially circumferentially aligned with one another in an unexpanded state, and desirably in a delivery configuration on a catheter. The unconnected peaks of each band become circumferentially displaced from the unconnected troughs of an adjacent serpentine circumferential band, and the unconnected troughs of each serpentine circumferential band become circumferentially displaced from the unconnected peaks of each serpentine circumferential band on expansion of the stent.

The invention is also directed to a stent comprising at least two serpentine bands including a first serpentine band and a second serpentine band. Each serpentine band has alternating peaks and troughs. The first serpentine band includes connected peaks and unconnected peaks, and the second serpentine band includes connected troughs and unconnected troughs. The first and second serpentine bands have an identical number of peaks. The peaks of the first serpentine band are substantially longitudinally aligned with the troughs of the second serpentine band when the stent is in an unexpanded state. The connected peaks are connected to the connected troughs. The unconnected peaks of each band become circumferentially displaced from the unconnected troughs of an adjacent band, and the unconnected troughs of each band become circumferentially displaced from the unconnected peaks of an adjacent band on expansion of the stent.

Desirably, the stent comprises a third serpentine band having alternating peaks and troughs. The first, second and third serpentine bands are arranged sequentially along the stent with the first serpentine band and the second serpentine band connected one to the other and defining a plurality of cells therebetween and the second serpentine band and the third serpentine band connected one to the other and defining a plurality of cells therebetween. The first, second and third serpentine bands have the same number of peaks.

More desirably, the stent has a first and second end region and a middle region extending therebetween wherein at least one of the first and second end regions of the stent has a different cell structure from the remainder of the stent. Optionally, the first and second end regions may have a cell structure which differs from one another.

Additional details and/or embodiments of the invention are discussed below.

BRIEF DESCRIPTION OF THE FIGURES

FIG. 6a shows a flat view of another inventive stent.

FIG. 6b shows an enlarged end portion of the stent of FIG. 6a.

DETAILED DESCRIPTION OF THE INVENTION

This invention may be embodied in many different forms. This description is an exemplification of the principles of the invention and is not intended to limit the invention to the particular embodiments illustrated.

For the purposes of this disclosure, unless otherwise indicated, identical reference numerals used in different figures refer to the same component.

Figure 5:
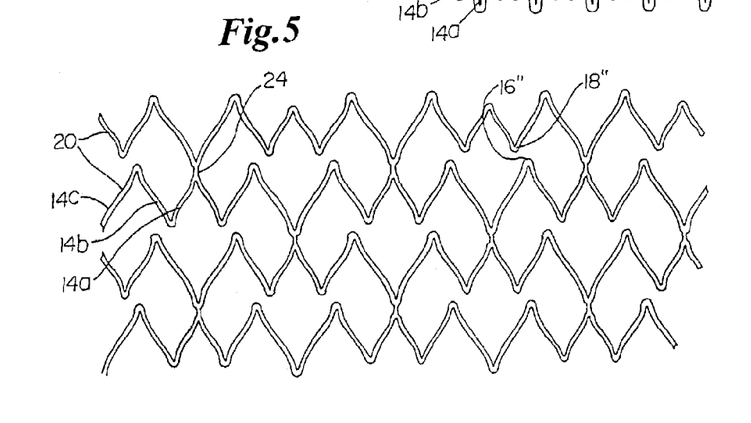
FIG. 5 shows a flat view of the stent of FIG. 4 in an expanded configuration.

Also, the phrase 'substantially circumferentially aligned' as used herein does not require perfect circumferential alignment. Rather, it requires that at least a portion of a peak be circumferentially aligned with a portion of a trough on an adjacent serpentine circumferential band. Examples of substantially circumferentially aligned peaks and troughs include but are not limited to facing peak 16' and trough 18' connected by longitudinal connector 24 shown in FIGS. 1a, 2 and 3 and facing peak 16b' and trough 18b' connected by longitudinal connector 24 shown in FIG. 5, as well as facing peak 16" and trough 18" shown in the circled regions of FIGS. 1–3.

Figure 1A:
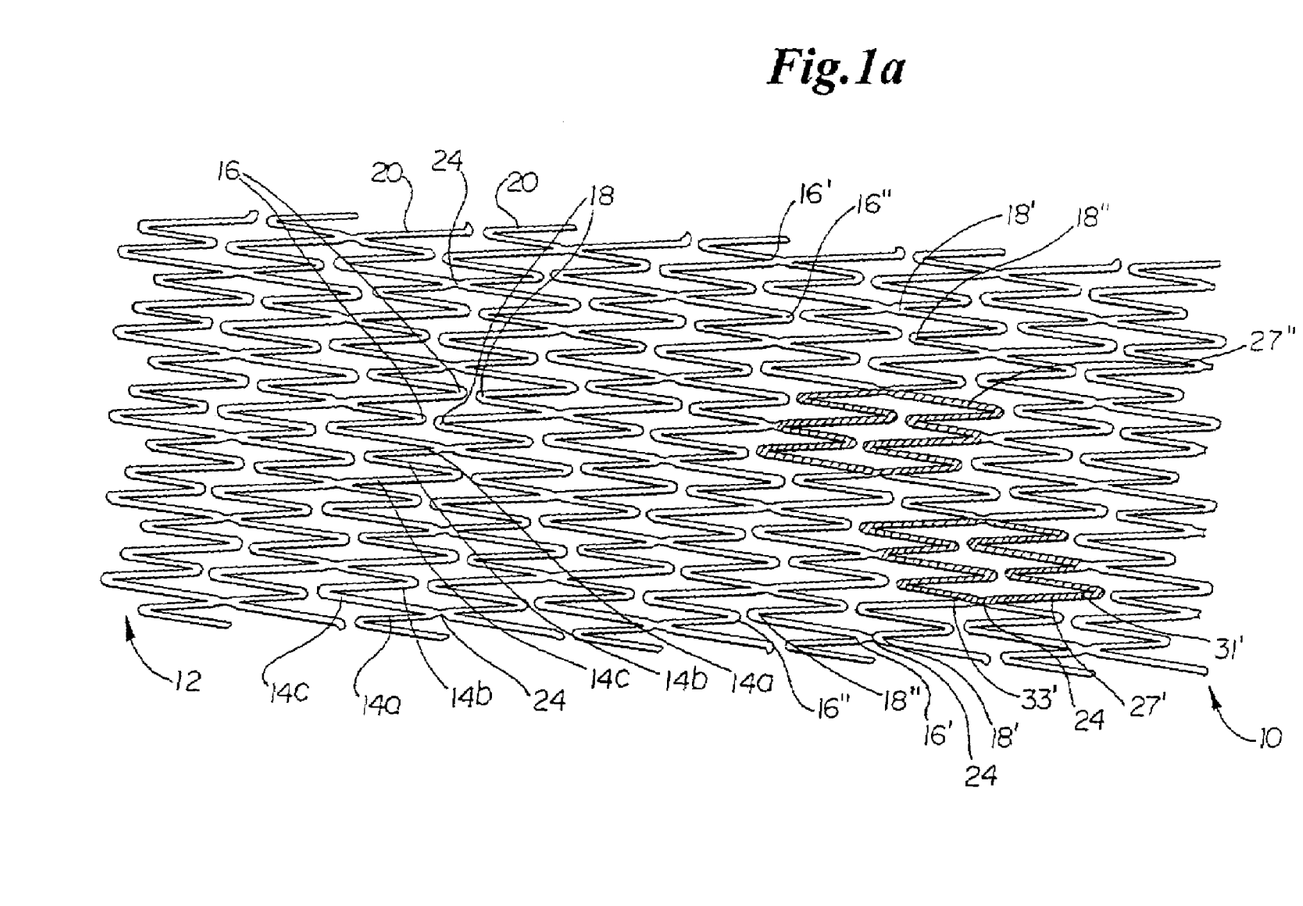
FIG. 1a shows a flat view of an inventive stent.
Figure 1B:
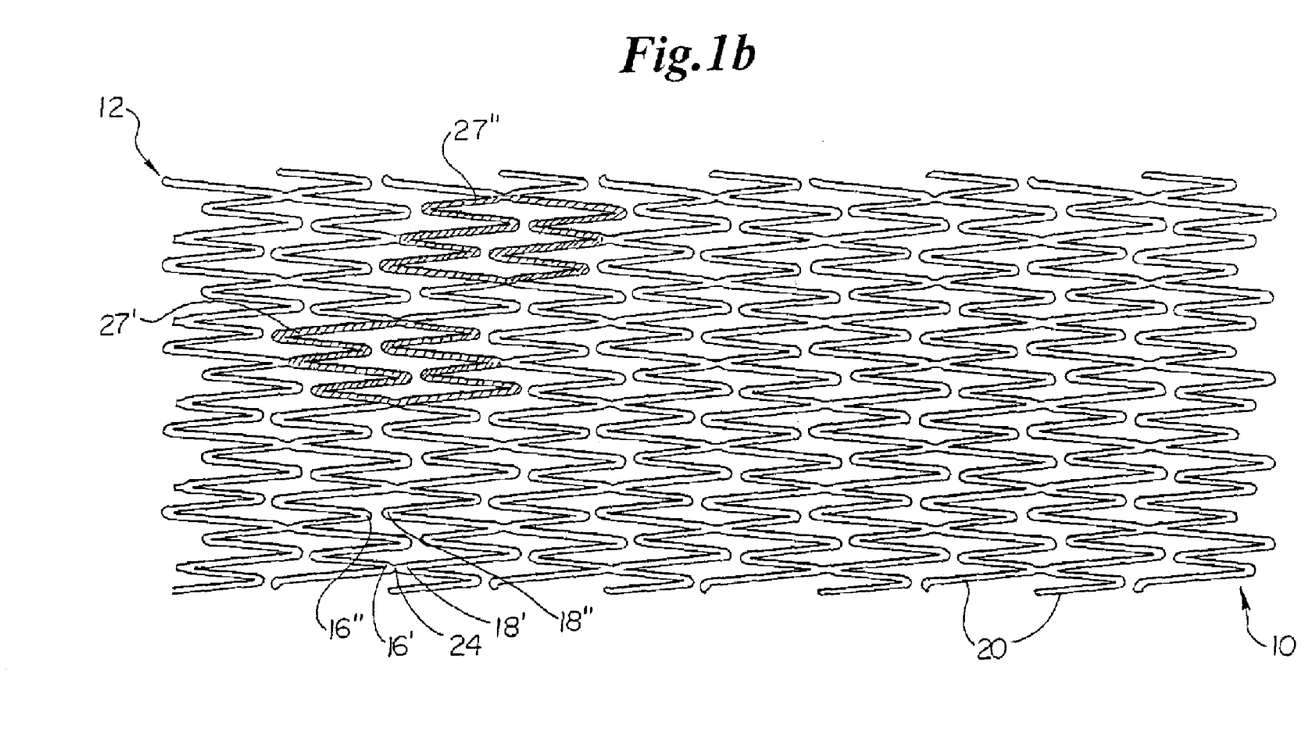
FIG. 1b shows a flat view of an inventive stent.
Figure 1C:
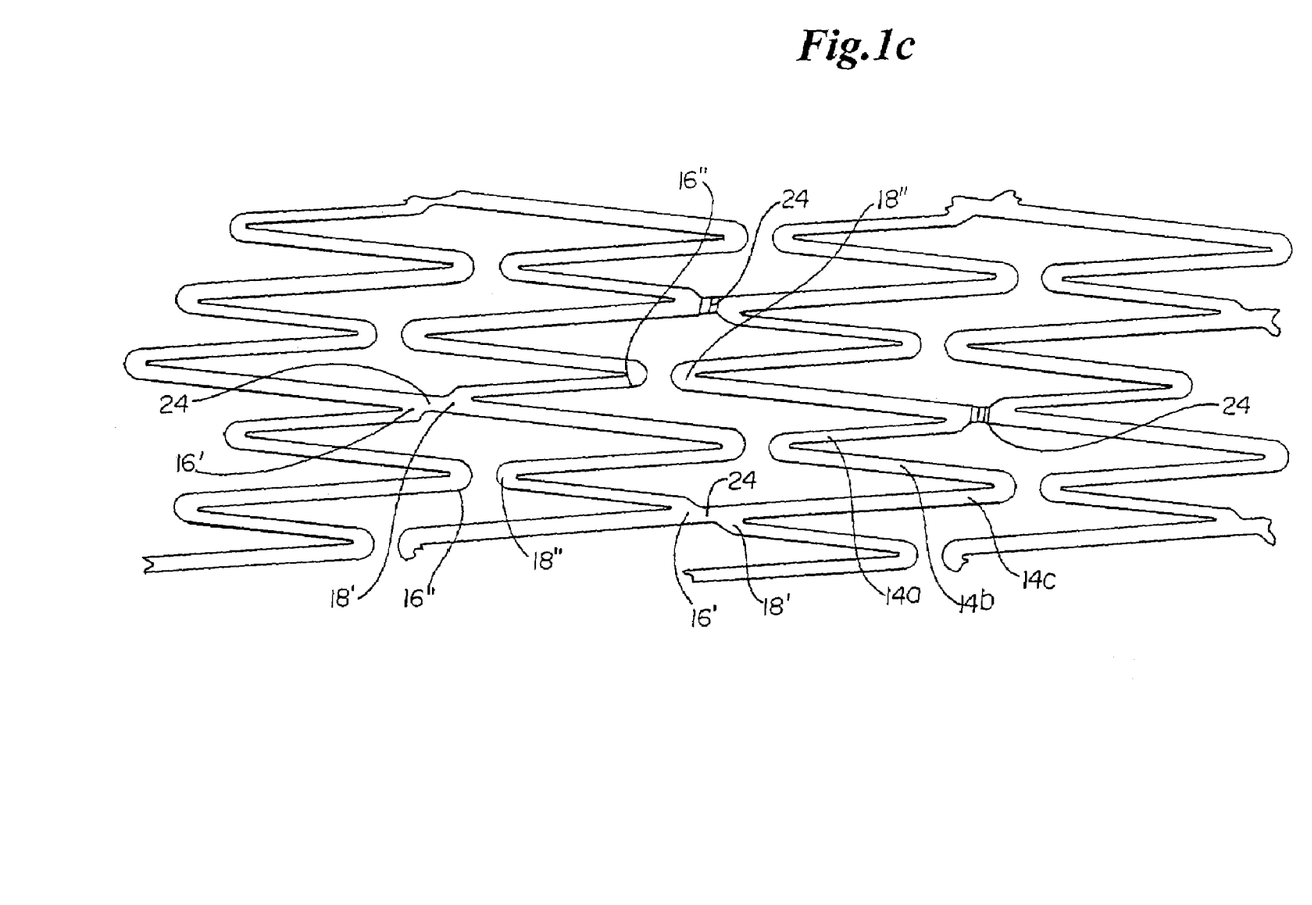
FIG. 1c shows an enlarged view of a portion of the inventive stent of FIG. 1b.
Figure 2:
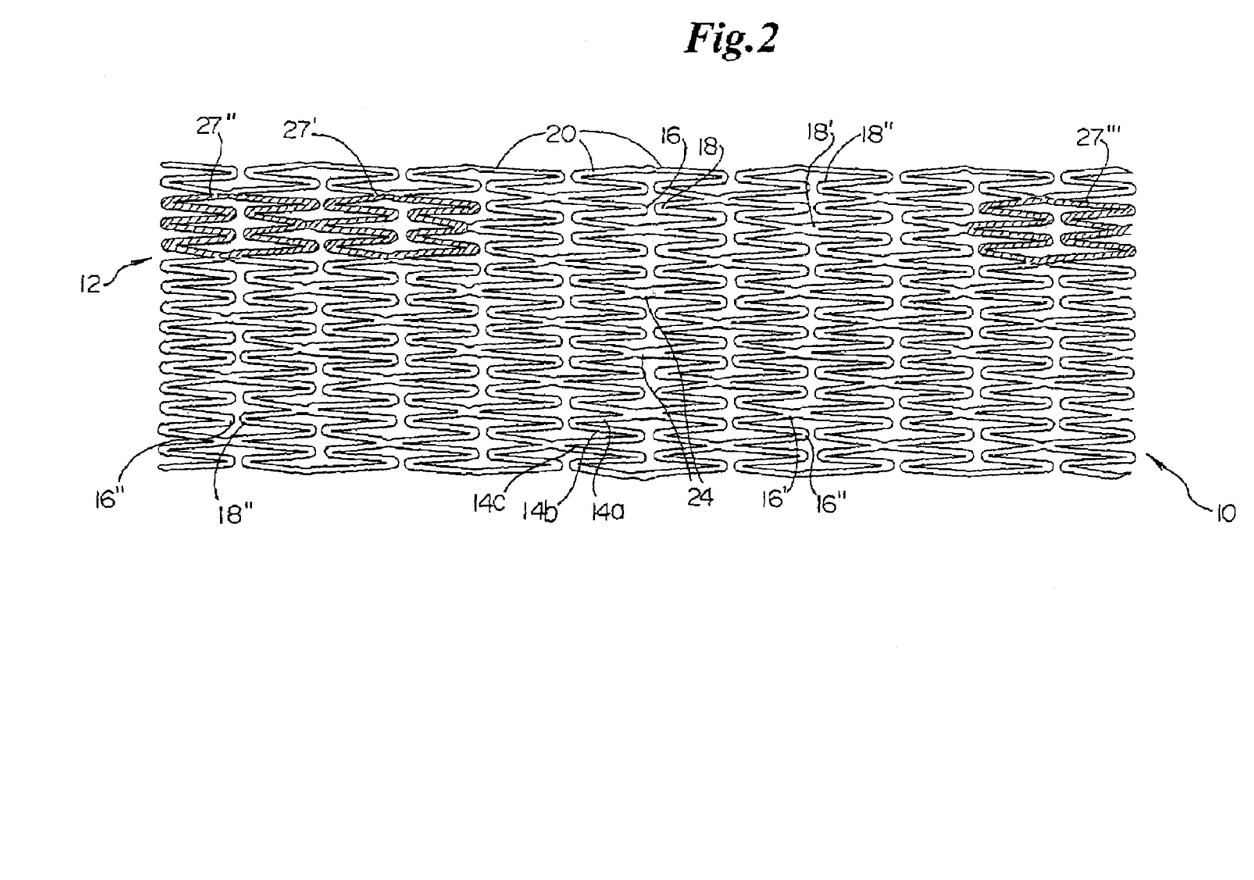
FIG. 2 shows a flat view of an inventive stent.
Figure 3:
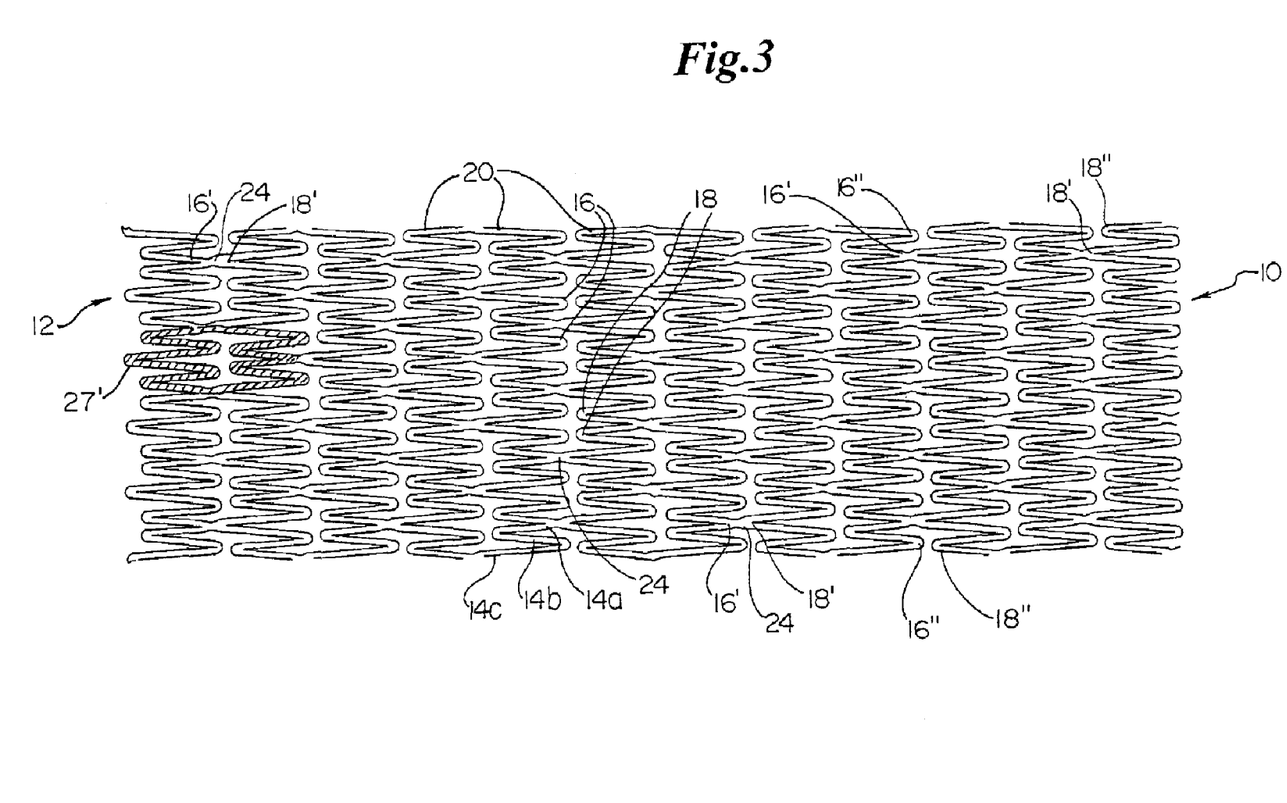
FIG. 3 shows a flat view of an inventive stent.

Further, the term 'longitudinally staggered' when used in reference to peaks or troughs within a serpentine circumferential band refers to peaks or troughs with the band which extend to different positions lengthwise along the length of the stent. Examples of longitudinally staggered peaks within a serpentine circumferential band include but are not limited to peaks 16' and 16" within a band as shown in FIGS. 13. Examples of longitudinally staggered troughs within a serpentine circumferential band include but are not limited to troughs 18' and 18" within a band as shown in FIGS. 1–3. Longitudinally aligned peaks or troughs extend to the same location lengthwise along the stent. Examples of longitudinally aligned peaks or troughs are shown in the proximal end and distal ends of the stent of FIG. 2. Other examples include all peaks 16' within a serpentine band.

The term 'distal' as used herein in reference to the distal end of a stent refers to the end of the stent which is inserted first into the body. The term 'proximal' as used herein in reference to the proximal end of a stent refers to the end of the stent which is inserted last into the body. It is within the scope of the invention that the orientation of any of the inventive stents disclosed herein can be reversed so that either end may be delivered into the body first.

In FIG. 1a, a flat view of an inventive stent is shown. The stent has a distal end 10 and a proximal end 12 and comprises a plurality of serpentine circumferential bands 20. Each band comprises a plurality of interconnected struts and includes struts of three different lengths. As shown, the first strut 14a is shorter and narrower than second strut 14b and third strut 14c. Third strut 14c is longer and wider that first strut 14a and second strut 14b. The struts 14a–c are arranged in a repeating pattern such that the circumferentially adjacent peaks 16 within each band 20 terminate at different longitudinal points along the stent and the circumferentially adjacent troughs 18 within each band 20 terminate at different longitudinal points along the stent.

Adjacent serpentine circumferential bands are connected to one another in at least one and desirably, as shown in FIG. 1a, a plurality of locations. In the stent of FIG. 1a, the connections between adjacent serpentine circumferential bands are in the form of longitudinal connectors 24 which extend between peaks 16 on one band and substantially circumferentially aligned troughs 18 on an adjacent band.

Desirably, circumferentially adjacent connectors 20 are separated by a path along one serpentine circumferential band which traverses at least two peaks of the serpentine circumferential band and by a path along the adjacent serpentine circumferential band which traverses at least two troughs of the adjacent serpentine circumferential band. The invention allows for more peaks or fewer and/or more troughs or fewer troughs between adjacent connectors of any of the embodiments disclosed herein.

The stent is further constructed so that in the unexpanded configuration, and desirably in a delivery configuration, peaks of one serpentine circumferential band are substantially circumferentially aligned with troughs of an adjacent serpentine circumferential band.

Because of the unequal strut pair lengths of strut pairs which are opposite one another on adjacent serpentine circumferential bands, on expansion of the stent unconnected peaks and troughs which were substantially circumferentially aligned with one another will be displaced circumferentially relative to one another.

In another embodiment of the invention, as shown in the flat in FIG. 1b, adjacent serpentine circumferential bands 20 are interconnected via a plurality of connectors 24 whose first and second ends are circumferentially and longitudinally offset from one another. Desirably, as shown in FIG. 1b, connectors 24 are substantially linear. Non-linear connectors, including curved connectors, connectors having curved portions and connectors having angled portions, may also used if space permits. Connectors 24 may be seen in greater detail in FIG. 1c which is an enlargement of a portion of the stent of FIG. 1b. The connectors are shown with hatch marks in FIG. 1c. Although connectors 24 are at an oblique angle relative to the longitudinal axis of the stent, they are, nevertheless, substantially parallel to the longitudinal axis of the stent. It is within the of the invention to provide embodiments in which connectors 24 are disposed at a more substantial angle relative to the longitudinal axis of the stent so that the connectors are not substantially parallel to the longitudinal axis of the stent. The connectors of FIG. 1b may also be longer, depending on the separation between adjacent serpentine circumferential bands.

In other respects, the stent of FIGS. 1b and 1c is similar to that of FIG. 1a. Both stents have three types of struts 14a–14c of increasing length and width. Both have connected pairs of peaks and trough 16' and 18' as well as unconnected pairs of substantially circumferentially aligned and unconnected peaks 16" and troughs 18". In both stents, the struts are distributed such that on expansion of the stent, unconnected but substantially circumferentially aligned peaks and troughs are displaced relative to one another about the circumference of the stent.

In another embodiment of the invention, as shown in the flat in FIG. 2, each serpentine circumferential band comprises three types of struts of different length, struts 14a–14c.

With the exception of the distal-most serpentine circumferential band, within a serpentine circumferential band, the peaks are arranged circumferentially in a repeat pattern of two longitudinally aligned adjacent peaks and one shorter peak adjacent to the two aligned peaks. Also, with the exception of the proximal-most serpentine circumferential band, within a serpentine circumferential band, the troughs are arranged circumferentially in a repeat pattern of two longitudinally aligned adjacent troughs and one longer trough adjacent to the two aligned troughs.

As with the stent of FIG. 1a, the struts within the serpentine circumferential bands are arranged such that when the stent is in an unexpaded state, peaks on one band are substantially circumferentially aligned with troughs on an adjacent substantially circumferential band. Upon expansion of the stent, peaks and troughs which were substantially circumferentially aligned with one another will be displaced circumferentially relative to one another.

The proximal-most and distal-most serpentine circumferential bands of the stent of FIG. 2 differ from that of FIG. 1a in that the troughs of the proximal-most serpentine circumferential band are aligned with another and the peaks of the distal-most serpentine circumferential band are aligned with another, unlike in the stent of FIG. 1a. Moreover, the peaks in the proximal-most serpentine circumferential band are arranged in a repeating pattern of two longer peaks followed by one shorter peak and the troughs in the distal-most serpentine circumferential band are arranged in a repeating pattern of one longer trough and two shorter troughs.

The stent of FIG. 2 is similar to the stent of FIG. 1a in that the number of connections between the adjacent serpentine circumferential bands is constant along the length of the stent. Also, the frequency of connections between the adjacent serpentine circumferential bands is constant along the length of the stent as is the spacing of the connections about the circumference of the stent.

Another inventive stent is shown in FIG. 3. The stent of FIG. 3 is similar to the stent of FIG. 2 but differs in that troughs in the proximal-most serpentine circumferential band are not longitudinally aligned with one another. Also, the peaks in the distal-most serpentine circumferential band are not longitudinally aligned with one another. Rather, the proximal-most and distal-most serpentine circumferential bands of the stent are of the same construction as the remainder of the serpentine circumferential bands in the stent.

Figure 4:
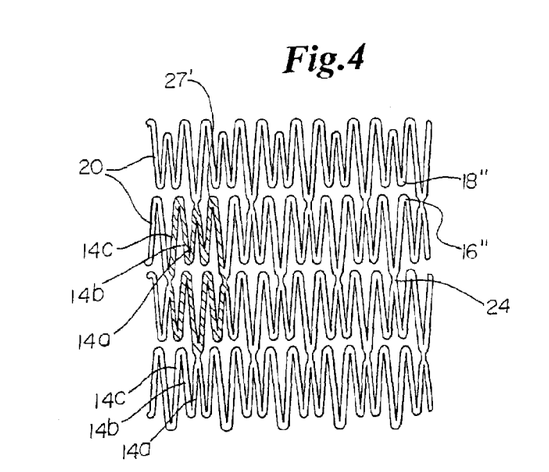
FIG. 4 shows a flat view of an inventive stent in an unexpanded configuration.

FIG. 4 shows a flat view of an inventive stent in an unexpanded configuration. In this figure the unconnected peaks 16" of each band proximal to the distal most band are substantially circumferentially aligned with the unconnected troughs 18" of an adjacent band 20. The struts 14a–c are of three lengths and widths. The stent of FIG. 4 is shown in an expanded configuration in FIG. 5. In the expanded configuration, unconnected peaks 16" and unconnected troughs 18" which were previously substantially circumferentially aligned with one another are now displaced circumferentially, relative to one another. A similar circumferential displacement between unconnected but substantially circumferentially aligned peaks and troughs occurs in the other stents disclosed herein as well.

Figures 6A, 6B:
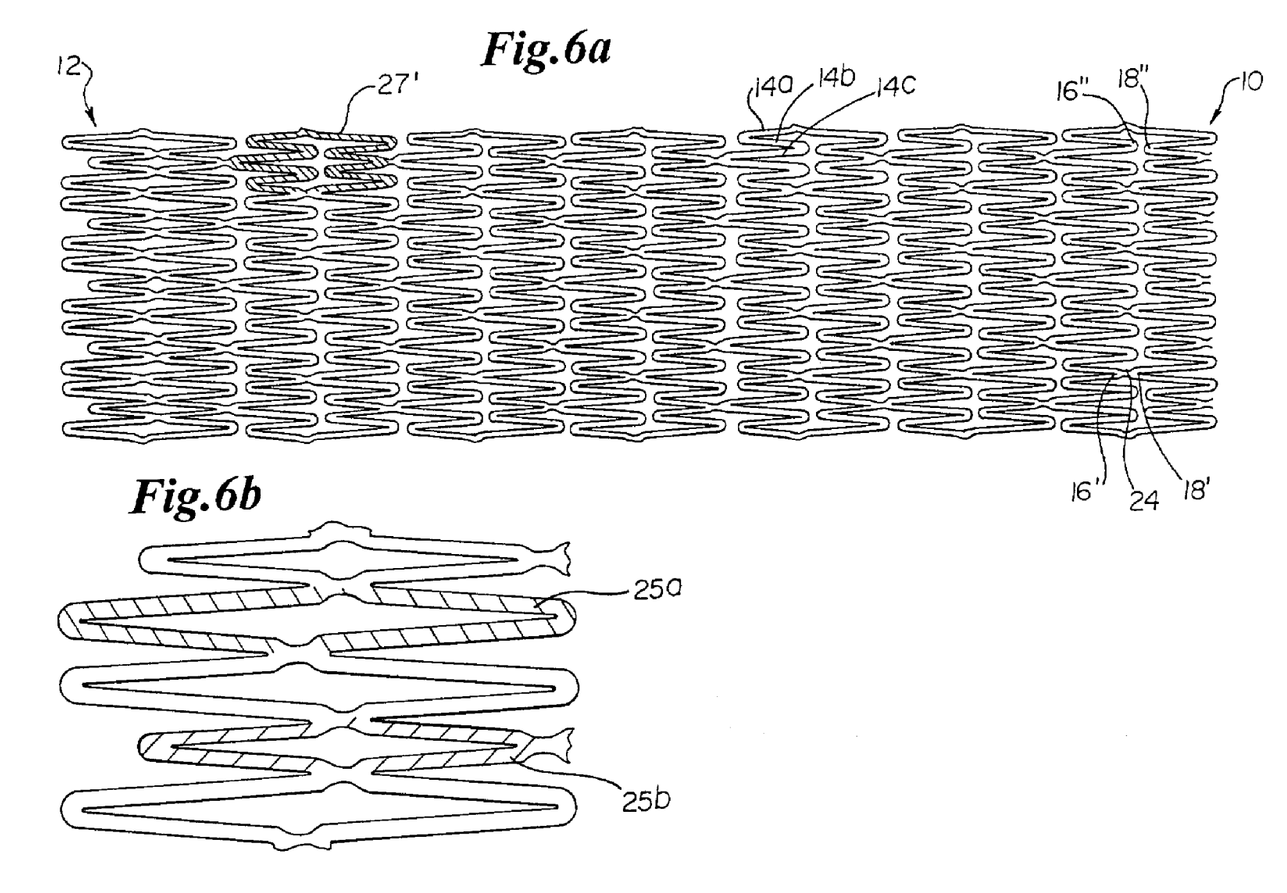

An inventive stent with special ends is shown in the flat in FIGS. 6a and 6b. Unlike with the stents of the previous figures, the stent of FIGS. 6a and 6b has an increased number of connectors extending between adjacent serpentine circumferential bands at the ends of the stent. Specifically, each peak on the proximal-most serpentine circumferential band is connected to a trough on the adjacent serpentine circumferential band and each trough on the distal-most serpentine circumferential band is connected to a peak on the adjacent serpentine circumferential band. The connectivity results in plurality of larger and smaller substantially diamond-shaped cells 25a and 25b (shown with hatching) which serves to stabilize the end of the stent.

The stent of FIGS. 6a and 6b may be modified in numerous ways. In one modification, only one end of the stent is provided with the additional connectors so that only one end of the stent has the large cell/small cell structure shown in FIGS. 6a and 6b. In another modification, at one or both ends of the stent three or more adjacent serpentine circumferential bands are interconnected with additional or fewer connectors as compared with the remainder of the stent. Thus, the resulting stent has multiple adjacent rows of large and small diamond cells at one or both ends of the stent. Also, the ratio of connectors to peaks may be other than the 1:1 ratio provided at the end of the stent of FIG. 6a and other than the ratio of 1:3 provided in FIG. 1a.

The stent of FIG. 1a is designed such that the expansion proceeds in the same way whether the stent is deployed from the proximal to the distal end or vice versa. The stents of FIGS. 2–6, on the other, expand differently depending on whether the stent is expanded from the proximal to the distal end or vice versa.

In the middle serpentine circumferential bands of the stent of FIG. 2, deployment from the distal end 10 of the stent results in the deployment of the unconnected peaks 16" of each serpentine circumferential band 20 before the deployment of the connected peaks 16'. Deployment from the proximal end 12 of the stent results in the deployment of the connected troughs 18' of each band 20 before the deployment of the unconnected troughs 18".

In the inventive stents disclosed herein, each serpentine circumferential band is characterized by a path length about the periphery of the stent. This path length corresponds to the length that the band would have if cut open and stretched out into a line. Desirably, as shown in FIGS. 1–6, each of the serpentine circumferential bands is of the same total pathlength. The invention also contemplates embodiment in which the serpentine bands are not all of the same pathlength. To the extent that the stent has pathlengths of different length, the different length pathways are desirably provided only at one or both ends of the stent.

In the inventive stents disclosed in FIGS. 1–6, the serpentine circumferential bands all have the same number of peaks and the same number of troughs. Although the invention also contemplates embodiments which include bands of different numbers of peaks and troughs, to the extent that such bands are present, it is desirable that they be present only at one or both ends of the stent.

To the extent that the stents of FIGS. 1–6 are considered to comprise serpentine circumferential bands, each of which comprises a plurality of interconnected struts, it is noted that all of the bands have the same number of struts. The invention also contemplates embodiments having the presence of some serpentine circumferential bands which have more or fewer struts than other of the serpentine circumferential bands. Desirably, however, the bands having different numbers of struts are provided only at one or both ends of the stent.

The inventive stents may also be considered to compromise a plurality of interconnected cells. As shown in FIG. 1a, the stent comprises a plurality of rows of interconnected cells 27' and 27". Cells 27' and 27" are identical in area and shape but extend in opposite helical directions about the longitudinal axis of the stent. Each cell is defined by first and second paths which are connected to one another by connectors. Cell 27' for example, has a first path 31' and a second path 33' connected by connectors 24. The first path forms a part of a serpentine circumferential band and the second path form a part of another serpentine circumferential band. In the embodiment of FIGS. 1–6, the first and second paths at the ends of a cell are of the same pathlength. The first and second paths of a cell also have the same number of struts. However, the arrangement of the struts in the first and second paths differ from one another resulting in peak-trough pairs within a cell which are substantially circumferentially aligned in an unexpanded state and desirably in a delivery configuration on a catheter and which are circumferentially displaced relative to one another on expansion of the stent.

In the embodiment of FIG. 1b, cells 27' and 27" are oriented in opposite helical directions about the longitudinal axis of the stent. In the embodiment of FIG. 2, three types of cells 27', 27" and 27'" are present as a result of the alignment of the peaks at one end and the troughs at the other end of the stent. In the embodiments of FIGS. 3 and 4, only a single type of cell 27' is present. In the embodiment of FIGS. 6a and 6b, cells 25a and 25b at the ends of the stent are substantially diamond shape whereas the remaining cells 27' are not substantially diamond shaped.

The inventive stents of FIGS. 1–6 allow for pairs of unconnected peaks and troughs on adjacent bands to be substantially aligned in an unexpanded state, and desirably in the delivery configuration, while allowing for the unconnected peaks and troughs to be displaced circumferentially relative to one another on expansion of the stent. This is achieved, using serpentine circumferential bands of equal path length and/or equal numbers of peaks, by arranging the struts of the stent such that the path length between a connected peak and a circumferentially adjacent connected peak on a first serpentine band is different from the path length along an adjacent serpentine band between the corresponding connected trough and the corresponding unconnected trough. Differently stated, the summed length of the two struts immediately circumferentially adjacent to a connected peak is different than the summed length of the two struts immediately adjacent the corresponding connected trough as the circumference of the stent is traversed in a given direction. By employing bands with the same number of peaks to achieve the displacement on expansion of the stent, the use of connectors which are substantially angled relative to the longitudinal axis may be avoided. Moreover, more uniform coverage of the vessel may be achieved as compared with stents having bands of differing numbers of peaks.

The invention is also directed to a stent having a proximal end and a distal end comprising a plurality of connected serpentine circumferential bands. Each serpentine band comprises a plurality of struts arranged in alternating peaks and troughs. Adjacent serpentine circumferential bands are connected via a plurality of longitudinal connectors extending between peaks on one serpentine circumferential band and troughs on the serpentine circumferential band adjacent thereto. The struts of the serpentine bands are arranged such that on expansion of the stent, peaks and troughs which are substantially circumferentially aligned with one another, but not connected with one another, on adjacent serpentine circumferential bands are circumferentially displaced from one another. Typically, each band comprises a repeating pattern of three or more struts of different lengths. The struts of different lengths are also typically of different widths. Desirably, the stent is constructed and arranged to be self-expanding.

The invention is also directed to a stent comprising at least one circumferential serpentine band disposed about a longitudinal axis, the serpentine band comprising a plurality of struts, adjacent struts connected one to the other, the serpentine band having alternating peaks and troughs, the serpentine band including at least three peaks which are circumferentially and longitudinally offset from one another. Typically, the stent will comprise a plurality of the circumferential serpentine band, adjacent circumferential serpentine bands connected to one another. Desirably, adjacent circumferential serpentine bands are connected to one another via two or more longitudinal connectors. More desirably, the stent is constructed such that unconnected peaks and troughs which are substantially circumferentially aligned prior to expansion of the stent are circumferentially displaced from one another on expansion of the stent.

The invention is also directed to a stent comprising at least one serpentine circumferential band which comprises a repeat pattern of three or more struts of different lengths. Desirably, the stent comprises a plurality of the serpentine band, adjacent bands connected to one another. The struts are arranged in a pattern of alternating peaks and troughs.

The invention is also directed to a stent comprising at least two serpentine bands including a first serpentine band and a second serpentine band, each serpentine band having alternating peaks and troughs, the first serpentine band including connected peaks and unconnected peaks, the second serpentine band including connected troughs and unconnected troughs. The peaks of the first serpentine band are substantially longitudinally aligned with the troughs of the second serpentine band when the stent is in an unexpanded state. The connected peaks are connected to the connected troughs with connectors, each of the connectors having two ends which are substantially longitudinally aligned with one another in at least the unexpanded state. The unconnected peaks of each band become circumferentially displaced from the unconnected troughs of an adjacent serpentine circumferential band, and the unconnected troughs of each serpentine circumferential band become circumferentially displaced from the unconnected peaks of each serpentine circumferential band on expansion of the stent.

The invention is also directed to a stent comprising at least two serpentine bands, such as that shown by way of non-limiting example in FIGS. 6a and 6b, including a first serpentine band and a second serpentine band. Each serpentine band has alternating peaks and troughs. The first serpentine band includes connected peaks and unconnected peaks, and the second serpentine band includes connected troughs and unconnected troughs. The first and second serpentine bands have an identical number of peaks. The peaks of the first serpentine band are substantially longitudinally aligned with the troughs of the second serpentine band when the stent is in an unexpanded state. The connected peaks are connected to the connected troughs. The unconnected peaks of each band become circumferentially displaced from the unconnected troughs of an adjacent band, and the unconnected troughs of each band become circumferentially displaced from the unconnected peaks of an adjacent band on expansion of the stent. Optionally, the first and second serpentine bands may be of different total pathlength about the stent.

Desirably, as shown in FIG. 6a, the stent comprises a third serpentine band having alternating peaks and troughs. The first, second and third serpentine bands are arranged sequentially along the stent with the first serpentine band and the second serpentine band connected one to the other and defining a plurality of cells therebetween and the second serpentine band and the third serpentine band connected one to the other and defining a plurality of cells therebetween. The first, second and third serpentine bands have the same number of peaks.

More desirably, as shown in FIGS. 6a and 6b, the stent has a first and second end region and a middle region extending therebetween wherein at least one of the first and second end regions of the stent has a different cell structure from the remainder of the stent. Optionally, the first and second end regions may have a cell structure which differs from one another.

The invention is also directed to helical stents. One or more helical bands may be provided where the peaks and troughs on it are arranged such that some of the peaks are substantially circumferentially aligned and connected to some of the troughs on an adjacent turn of the helical band or on an adjacent helical band and other substantially circumferentially aligned peaks and troughs on adjacent bands or adjacent turns of a band are not connected to one another. On expansion of the stent, the non-connected substantially circumferentially aligned peaks and troughs are circumferentially displaced from one another. This may be achieved with an appropriate arrangement of struts.

Any of the inventive stents disclosed herein may also be provided in a 'jelly roll' configuration. For example, the flat pattern of FIG. 1 may be rolled into a tube without securing the longitudinal edges to one another. Such a stent would be deployed by unrolling and expansion of the cells or bands which extend about the longitudinal axis of the stent. An example of such a stent is disclosed in WO0132099.

The inventive stents disclosed herein may also be provided in an embodiments in which the longitudinal connectors may be shorter or longer than those shown in FIG. 1a or any of the other figures disclosed herein. For example, in one embodiment, where adjacent bands have the same number of peaks, facing peaks and troughs which are connected to one another may abut one another and the connector may be in the form of a small weld or an overlap region between the facing peak and trough. Also, connector which are curved may be used to connect facing peaks and troughs. The connectors may also be located offset from the peaks and troughs.

The invention is also directed to stents such as those disclosed herein with sidebranch access. Such a stent may be provided by omitting one or more struts in one or more desired regions of the stent. Sidebranch access may also be provided by omitting a first serpentine band and providing connectors between some, but not all of the peaks and troughs of the resulting adjacent second serpentine bands. Sidebranch access may further be achieved in any of the inventive stents disclosed herein by alternating the location of connectors between adjacent serpentine bands. For example, where it is desirable to provide for sidebranch access, fewer connections between adjacent bands may be provided. Sidebranch access may also be provided by including adjacent serpentine bands of different total pathlength. In such a case, it is desirable although not necessary that the adjancent serpentine bands have the same number of peaks.

The inventive stents disclosed herein may also be used in bifurcated stents. The trunk and/or any of the branches may be provided with stents having the novel designs disclosed herein.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the struts, serpentine bands and/or longitudinal connectors may increase or decrease along portions of the stent or along the entire length of the stent. The amplitude and/or wavelength of several successive first serpentine bands may remain constant while the width and/or thickness of the successive first serpentine bands decreases. Similarly, the amplitude and/or wavelength of several successive second serpentine bands may remain constant while the width and/or thickness of the successive second serpentine bands decreases. In other embodiments of the inventive stents disclosed herein, the amplitude and/or wavelength of several successive first serpentine bands may decrease or increase while the width and/or thickness of the successive first serpentine bands remains constant. Similarly, the amplitude and/or wavelength of several successive second serpentine bands may or decrease or increase while the width and/or thickness of the successive second serpentine bands remain constant. The amplitude of the stent could also be increased or decrease along with the thickness and/or width of the stent.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and welding the sheet, by electrode discharge machining, or by molding the stent with the desired design.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel titanium alloys generically known as "nitinol", platinum/tungsten alloys and titanium alloys. The invention also contemplates the use of more than one material in the inventive stents. For example, the first serpentine band and the second serpentine band may be made of different materials. Optionally, the connectors may be made of a different material than the first and/or second serpentine bands.

The inventive stents desirably are provided in self-expanding form. To that end, they may be constructed from shape memory materials including Nitinol. The self-expanding embodiments of the invention allow for a controlled expansion of the stent as explained below. Typically, self-expanding stents are restrained on a catheter in an unexpanded configuration via a sheath. As the sheath is withdrawn, the newly freed portions of the stent will self-expand. Because the peaks within a serpentine cylindrical bands extend to different longitudinal extent, each serpentine circumferential band will be freed from the sheath in several waves—the first wave of peaks, corresponding to the longest peaks will expand first, followed by a wave of peaks which are shorter expanding until the serpentine is expanded.

The inventive stents may also be provided in balloon expandable form, or as a hybrid, having self-expanding characteristics and balloon expandable characteristics.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum tungsten, palladium, platinum iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids.

Portions of the interior and/or exterior of the stent may be coated or impregnated with the compound. Mechanical retention devices may also be used to maintain the stent on the balloon during delivery.

The inventive stents may also be used as the framework for a graft or may have a liner disposed therein. Suitable coverings and liners include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers.

The inventive stents may find use in coronary arteries, renal arteries, peripheral arteries including illiac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate.

The invention is also directed to stent delivery catheters with stents such as those disclosed herein disposed about a portion of the catheter.

The invention is also directed to methods of delivering any of the stents disclosed herein. The methods comprise delivering a catheter with an inventive stent disclosed herein disposed thereabout to a desired bodily location and expanding the stent or allowing the stent to expand. In the latter case, the stent is self-expanding and a sheath which restrains the stent is removed from about the stent. As the sheath is removed, waves of peaks from a given serpentine circumferential band are freed to self-expand. Upon deployment of the stent, the catheter is removed from the body.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

In addition to the specific embodiments claimed below, the invention is also directed to other embodiments having any other possible combination of the dependent features claimed below. As such, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 1, claim 5 may be taken as alternatively dependent from claims 1–4, claim 6 may be taken as alternatively dependent from claims 1–5; etc.).

The above Examples and disclosure are intended to be illustrative and not exhaustive. These examples and this description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent comprising:
    at least two serpentine circumferential bands including a first serpentine circumferential band and a second serpentine circumferential band, each serpentine circumferential band having alternating peaks and troughs,
    there being a plurality of unconnected peak-trough pairs, each unconnected peak-trough pair comprising a peak on the first serpentine circumferential band and a trough on the second serpentine circumferential band which is substantially circumferentially aligned with the peak when the stent is in an unexpanded configuration, the trough not connected to the peak,
    there being a plurality of unconnected peak-trough pairs, each connected peak-trough pair comprising a peak on the first serpentine circumferential band and a trough on the second serpentine circumferential band which is substantially circumferentially aligned with the peak when the stent is in an unexpanded configuration, the trough connected to the peak,
    the distance along the first serpentine circumferential band between each peak of a connected peak-trough pair and an adjacent peak of an unconnected peak-trough pair differing from the distance along the second serpentine circumferential band between the trough of the connected-trough pair and an adjacent trough of an unconnected peak-trough pair, the adjacent peak substantially opposite the adjacent trough,
    the peaks of the serpentine circumferential bands including short peaks and long peaks, the long peaks extending distally beyond the short peaks in the serpentine circumferential band and the troughs of the serpentine circumferential bands including short troughs and long troughs, the long troughs extending proximally beyond the short troughs in the serpentine circumferential band, the long and short peaks of a serpentine circumferential band arranged in a repeating pattern of two long peaks and one short peak, the long and short troughs of a serpentine circumferential band arranged in a repeating pattern of two short toughs and one long trough.

2. The stern of claim 1 wherein the first and second serpentine circumferential bands are connected to one another via a plurality of longitudinal connectors.

3. The stent of claim 1 comprising three or more of the serpentine circumferential bands, adjacent serpentine circumferential bands connected one to the other, there being a plurality of unconnected peak-trough pairs along adjacent serpentine circumferential bands, each unconnected peak-trough pair comprising a peak on one serpentine circumferential band and a trough on the adjacent serpentine circumferential band which is substantially circumferentially aligned with the peak when the stent is in an unexpanded configuration, the trough not connected to the peak, there being a plurality of connected peak-trough pairs along adjacent serpentine circumferential bands, each connected peak-trough pair comprising a peak on one serpentine circumferential band and a trough on the adjacent serpentine circumferential band which is substantially circumferentially aligned with the peak when the stent is in an unexpanded configuration, the trough connected to the peak, the distance along a serpentine circumferential band between each peak of a connected peak-trough pair and an adjacent peak of an unconnected peak-trough pair differing from the distance along the adjacent serpentine circumferential band between the trough of the connected-trough pair and an adjacent trough of an unconnected peak-trough pair, the adjacent peak substantially opposite the adjacent rough.

4. The stent of claim 3 wherein the adjacent serpentine circumferential bands are connected to one another via a plurality of longitudinal connectors.

5. The stern of claim 4 wherein circumferentially adjacent connected peak-trough pairs are separated by at least two substantially circumferentially aligned peaks and troughs.

6. The stout of claim 1 wherein circumferentially adjacent connected peak-trough pairs are separated by at least two substantially circumferentially aligned peaks and troughs.

7. The stent of claim 1 wherein the serpentine circumferential bands are each constructed of a repeating pattern of struts of at least three different lengths.

8. The stent of claim 7 wherein the longest of the struts is wider than the other struts.

9. The stent of claim 8 wherein the shortest of the struts is narrower than the other struts.

10. The stent of claim 1 constructed and arranged to be self-expanding.

* * * * *

UNITED STATES PATENT AND TRADEMARK OFFICE
CERTIFICATE OF CORRECTION

PATENT NO. : 7,223,283 B2  Page 1 of 1
APPLICATION NO. : 10/269111
DATED : May 29, 2007
INVENTOR(S) : Paul Chouinard It is certified that error appears in the above-identified patent and that said Letters Patent is hereby corrected as shown below:

In column 14, line 34, claim 1, delete "unconnected" and insert --connected-- therefor.

Signed and Sealed this

Thirty-first Day of August, 2010

David J. Kappos
*Director of the United States Patent and Trademark Office*